United States Patent [19]

Bauer, Jr. et al.

[11] Patent Number: 5,208,370
[45] Date of Patent: May 4, 1993

[54] METHOD OF REDUCING IMPURITIES IN AQUEOUS ACRYLIC MONOMER SOLUTIONS

[75] Inventors: William Bauer, Jr., Huntingdon Valley; Nelson I. Quirós, North Wales, both of Pa.

[73] Assignee: Rohm and Haas Co., Philadelphia, Pa.

[21] Appl. No.: 872,278

[22] Filed: Apr. 22, 1992

[51] Int. Cl.$^5$ .............................. C07C 51/42
[52] U.S. Cl. .................................... 562/600
[58] Field of Search ............................ 562/600

[56] References Cited

U.S. PATENT DOCUMENTS

| | | | |
|---|---|---|---|
| 3,674,651 | 7/1972 | Otsuti | 562/600 |
| 3,725,208 | 4/1973 | Maezawa et al. | |
| 3,893,895 | 7/1975 | Dehnert et al. | |
| 4,828,652 | 5/1989 | Schropp | 562/600 |

FOREIGN PATENT DOCUMENTS

| | | |
|---|---|---|
| 102642 | 3/1984 | European Pat. Off. |
| 8141614 | 12/1974 | Japan |
| 62-04521 | 1/1984 | Japan |
| 6404505 | 12/1985 | Japan |
| 61-21855 | 9/1986 | Japan |

*Primary Examiner*—Michael L. Shippen
*Attorney, Agent, or Firm*—Terence P. Strobaugh; David T. Banchik

[57] ABSTRACT

The present invention provides a method of reducing the levels of protoanemonin present in aqueous monomer solutions by adding an effective amount of one or more para-phenylenediamines having the formula:

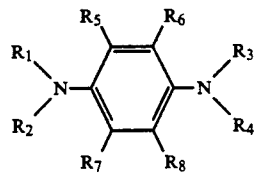

wherein $R_1$, $R_2$, $R_3$ and $R_4$ are the same or different radical selected from hydrogen, methyl, ethyl, n-propyl, iso-propyl, phenyl or methoxyphenyl with the proviso that at least one of $R_1$, $R_2$, $R_3$ and $R_4$ is hydrogen; $R_5$, $R_6$, $R_7$ and $R_8$ are the same or different radical selected from hydrogen, methyl, ethyl, n-propyl, iso-propyl, methoxy or ethoxy with the proviso that at least one of $R_5$, $R_6$, $R_7$ and $R_8$ is hydrogen; and salts thereof.

17 Claims, No Drawings

METHOD OF REDUCING IMPURITIES IN AQUEOUS ACRYLIC MONOMER SOLUTIONS

FIELD OF THE INVENTION

The present invention is directed to a method of reducing impurities in aqueous monomer solutions. In particular, the present invention is directed to a method of reducing the level of 5-methylene-2(5H)-furanone, also known as protoanemonin, in aqueous monomer solutions where protoanemonin is present as an impurity.

BACKGROUND OF THE INVENTION

In the production of certain monomers, ethylenically unsaturated hydrocarbons are oxidized, usually in the presence of a suitable catalyst to form the desired monomer. For example, one method for producing acrylic acid is by vapor-phase oxidation of propylene or acrolein in the presence of a catalyst. Similarly, the methacrylic acid can be produced by vapor-phase oxidation of isobutylene, tertiary butanol, tertiary-butyl methyl ether, methacrolein or isobutyraldehyde. The products which result from these processes are aqueous solutions of monomer which are contaminated with undesirable by-products. The aqueous monomer solutions are then extracted with a suitable solvent to recover the monomer. The organic phase containing the monomer is then stripped of the solvent in a solvent-separation step to obtain the monomer product. The low-boiling impurities are then distilled from the monomer product. Finally, the monomer product is distilled to separate high-boiling impurities.

Some of the impurities in the monomer product include acrolein, methacrolein, propionic acid, acetic acid, acetaldehyde, maleic acid, benzoic acid, terephthalic acid, and toluic acid. These by-products, or impurities, can impart color to the product or can act as polymerization inhibitors. Additional processing steps, usually distillations, are required to reduce or remove these impurities, thereby increasing the cost of manufacturing pure monomer products.

One of the impurities formed as a by-product in the production monomers such as acrylic acid and methacrylic acid is protoanemonin:

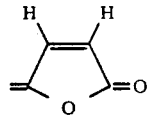

The art has long sought an efficient and cost effective method of reducing the levels of protoanemonin in monomer solutions. Three general approaches have emerged: treating the aqueous monomer solution resulting from the vapor-phase oxidation, treating the extracted monomer/solvent mixture, and treating the glacial monomer.

A representative method of reducing by-products by treating an aqueous monomer solution is described in Japanese patent 62-045219. The method disclosed therein requires treating an aqueous acrylic acid solution with bisulfite, such as an alkali metal bisulfite or ammonium bisulfite before performing the extraction. Japanese patent 62-045219 discloses that this method is effective for reducing the levels of acrolein, propionic acid, acetic acid, acetaldehyde, carbon monoxide, carbonic acid gas, maleic acid and aromatic acids such as benzoic acid and terephthalic acid. These references do not disclose or suggest reduction of protanemonin levels.

A representative method of reducing by-products by treating an extracted monomer/solvent mixture, is described in European patent application 102642. The method disclosed therein requires treating an extracted methacrylic acid/solvent mixture with an aqueous bisulfite solution, such as an alkali metal bisulfite or ammonium bisulfite, followed by a separation step. European patent application 102642 discloses that this method is effective for reducing the levels of protoanemonin in methacrylic acid. This reference does not disclose or suggest reduction of protanemonin levels by treating the aqueous monomer solution.

Japanese patent application 61-218556 discloses a method of treating either an extracted acrylic acid/solvent mixture or a glacial acrylic acid to lower the levels of impurities. Japanese patent 64-004505 discloses a method of treating either an extracted methacrylic acid/solvent mixture or a glacial methacrylic acid to lower the levels of impurities. These references disclose that after the addition of bisulfite which is introduced into the aqueous monomer solution, the addition of hydrazine compounds to the extracted monomer/solvent mixture or to the glacial monomer, further reduces the levels of acrolein, propionic acid, acetic acid, formic acid, acetaldehyde, formaldehyde, carbon oxides, maleic acid, furfural, protoanemonin, and aromatic acids such as benzoic acid and terephthalic acid in the monomer product. These references do not disclose or suggest reduction of protanemonin levels by treating the aqueous monomer solution.

Japanese patent 81-41614 discloses a method of reducing the level of protoanemonin in acrylic acid by treating either the aqueous acrylic acid solution resulting from the vapor-phase oxidation, the extracted acrylic acid/solvent mixture, or the glacial acrylic acid. The method disclosed therein requires the addition of 0.5% to 1% by weight of the solution to which it is being added of a nitrous acid salt, nitrogen oxide or nitrobenzene, and a polymerization inhibitor.

U.S. Pat. No. 3,725,208 is directed to a method of treating glacial acrylic acid to reduce the levels of aldehyde impurities. This patent discloses that the addition of sulfuric acid, hydrazine, phenylhydrazine, aniline, monoethanolamine, ethylenediamine or glycine to glacial acrylic acid followed by a distillation results in a reduction in the level of aldehyde impurities in the acrylic acid.

U.S. Pat. No. 3,893,895 is directed to a method of treating glacial 1,2-unsaturated carboxylic acids to reduce the level of carbonyl compounds which are present as impurities. The carbonyl compounds include acrolein formaldehyde, methacrolein, crotonaldehyde, acetaldehyde, hexen-2-al, acetone and furfural. According to the disclosure of the U.S. Pat. No. 3,893,895, the levels of these compounds in the 1,2-unsaturated carboxylic acids are reduced by treating the glacial acid with an amine and distilling the mixture. The amines which are disclosed as being useful are inorganic amines, primary and secondary aliphatic and aromatic amines, such as hydrazine, hydroxylamine, 1,2-ethanolamine, 1,2-ethylenediamine, octyl amine, 1,3-propanolamine, 1,2-propanolamine, octadecyl amine, aniline, p-phenylenediamine, o-phenylenediamine, 1,2- dianilinoethane, alpha naphthyl amine, beta naphthyl amine, p-methyl aniline, o-methyl aniline, N-methyl aniline, semi-carbazide, phenyl hydrazine, and 2,4-dimethyl aniline. This reference does not disclose or suggest reduction of protanemonin levels.

SUMMARY OF THE INVENTION

It is an object of the present invention to provide a method of reducing the level of protoanemonin in aqueous monomer solution by adding to the aqueous monomer solution an effective amount of one or more para-phenylenediamines having the following formula:

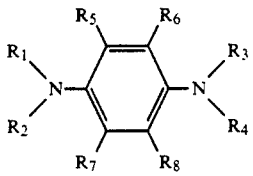

wherein $R_1$, $R_2$, $R_3$ and $R_4$ are the same or different radical selected from hydrogen, methyl, ethyl, n-propyl, iso-propyl, phenyl or methoxyphenyl with the proviso that at least one of $R_1$, $R_2$, $R_3$ and $R_4$ is hydrogen; $R_5$, $R_6$, $R_7$ and $R_8$ are the same or different radical selected from hydrogen, methyl, ethyl, n-propyl, iso-propyl, methoxy or ethoxy with the proviso that at least one of $R_5$, $R_6$, $R_7$ and $R_8$ is hydrogen; and salts thereof.

It is a further object of the present invention to reduce the levels of protoanemonin in aqueous acrylic acid solutions and aqueous methacrylic acid solutions by adding one or more para-phenylenediamines (I, supra) to those solutions in an amount effective to reduce the levels of protoanemonin.

DETAILED DESCRIPTION OF THE INVENTION

Adding one or more para-phenylenediamines (I, supra) to aqueous monomer solutions reduces the level of protoanemonin. Preferred para-phenylenediamines of formula I are those wherein at least two of $R_1$, $R_2$, $R_3$ and $R_4$ are hydrogen and wherein at least two of $R_5$, $R_6$, $R_7$ and $R_8$ and are hydrogen. Examples of para-phenylenediamines useful in the present invention include 1,4 phenylenediamine (referred to hereinafter as p-PD), N,N-dimethyl-1,4-phenylenediamine, N-(4-methoxyphenyl)-1,4-phenylenediamine, 2,5-dimethyl-1,4-phenylenediamine, 2-methoxy-N⁴-phenyl-1,4-phenylenediamine and 2-methoxy-1,4-phenylenediamine.

Salts of the one or more para-phenylenediamines (I, supra) may also be added to the aqueous monomer solution to reduce the level of protoanemonin. Suitable salts include the hydrogen halide, sulfate and hydrogen sulfate salts thereof such as 1,4-phenylenediamine hydrochloride, 1,4-phenylenediamine dihydrochloride, N-(4-methoxyphenyl)-1,4-phenylenediamine hydrochloride, N,N-dimethyl-1,4-phenylenediamine hydrochloride, N,N-dimethyl-1,4-phenylenediamine sulfate and 2-methoxy-1,4-phenylenediamine sulfate hydrate. Unless specifically stated otherwise, the salts of the para-phenylenediamines may be either the partial or complete salts, i.e. one or both of the amines in the diamine may be a salt.

The para-phenylenediamines (I, supra) may be employed in their pure form, which, depending on the melting point, is either a solid or a liquid. Furthermore, the para-phenylenediamines useful in the present invention can be employed as a solution. Solutions may be prepared by dissolving one or more para-phenylenediamines (I, supra) in a suitable solvent including water, aqueous acid and base solutions, and organic solvents. It may be desirable to dissolve the one or more para-phenylenediamines in a sample of the monomer being purified. If the one or more para-phenylenediamines (I, supra) are dissolved in monomer, the resulting solution should be added to the aqueous monomer solution quickly to minimize the extent to which the para-phenylenediamines might react with the monomer. Preferably, the one or more para-phenylenediamines (I, supra) are employed as a solid or an aqueous solution.

The one or more para-phenylenediamines (I, supra) are added to aqueous monomer solutions contaminated with protoanemonin, such as, for example, aqueous solutions of acrylic acid or methacrylic acid. It is beneficial to provide agitation following the addition of the one or more para-phenylenediamines. The aqueous monomer solutions may range from about 10 percent by weight to about 95 percent by weight monomer. Preferably, the aqueous monomer solution is from about 15 percent by weight to about 90 percent by weight monomer and most preferably from about 20 percent to about 65 percent by weight monomer.

Because of the relative quantities of para-phenylenediamine and aqueous monomer solution, the preferred method of the present invention is to add the one or more para-phenylenediamines (I, supra) to the aqueous monomer solution. However, other methods will be apparent to those skilled in the art of bringing the one or more para-phenylenediamines (I, supra) into contact with the aqueous monomer solutions contaminated with protoanemonin. These other methods are embraced within this invention and are considered functionally equivalent to addition.

The one or more para-phenylenediamines (I, supra) may be added to the aqueous monomer system at a temperature up to the boiling point of the aqueous monomer solution. Preferably, the one or more para-phenylenediamines (I, supra) are added to the aqueous monomer solution at a temperature of from about 10° C. to about 90° C., most preferably from about 20° C. to about 60° C. These temperature ranges are preferred because they may not require the aqueous monomer solution resulting from the vapor phase oxidation to be heated or cooled. The temperature will affect the rate at which the para-phenylenediamine will react with the protoanemonin. At higher temperatures, the reaction may be complete in 10 minutes to 2 hours, whereas the lower temperatures may require 3 to 10 hours.

The one or more para-phenylenediamines (I, supra) are added to the aqueous monomer solution in an amount effective to reduce the level of protoanemonin. Generally, the para-phenylenediamines are added at a level of from about 0.3 to about 400 molar equivalents based on the level of protoanemonin present. Protoanemonin is usually present in the aqueous monomer solution at levels of from about 5 to 400 parts per million (ppm). Preferably, the para-phenylenediamines are added to the monomer solution at a level of from about 0.5 to about 300 and most preferably from about 0.7 to about 200 molar equivalents based on the level of protoanemonin present. The para-phenylenediamines which are considered effective are those which, when added to an aqueous monomer solution containing protoanemonin as an impurity, reduce the level of protoanemonin by 10 percent or more when the molar ratio of para-phenylenediamine to protoanemonin is less than 30:1, preferably 20 percent or more when the molar ratio of para-phenylenediamine to protoanemonin is less than 30:1.

The following procedure was used to evaluate the effectiveness of various levels of different types of phenylenediamines at reducing the level of protoanemonin present in a 32 percent by weight aqueous solution of acrylic acid:

To a 5-liter round bottom flask equipped with a mechanical stirrer, condenser and heating mantle were added 3.0 liters of aqueous acrylic acid solution prepared by vapor phase oxidation of propylene. The acrylic acid content of the solution was 32 percent by weight. The protoanemonin (PTA) level of the aqueous acrylic acid solution was determined by high pressured liquid chromatography (HPLC) and is reported in parts per million based on the aqueous monomer solution. The aqueous acrylic acid solution was stirred vigorously and the temperature was maintained at a predetermined level. To the stirred aqueous acrylic acid solution was added the phenylenediamine. After three hours, the protoanemonin level was determined by HPLC. The data for several trails following this procedure appear in Table 1, below.

TABLE 1

| Example | Molar Ratio p-PD:PTA | Temp. (°C.) | PTA initial (ppm) | PTA final (ppm) | PTA reduction (%) |
|---|---|---|---|---|---|
| 1 | 0.98:1 | 30 | 55 | 28 | 49 |
| 2 | 1.80:1 | 30 | 55 | 28 | 49 |
| 3 | 1.93:1 | 90 | 49 | 31 | 37 |
| 4 | 2.29:1 | 60 | 45 | 27 | 40 |
| 5 | 3.00:1 | 30 | 44 | 16 | 63 |
| 6 | 3.25:1 | 30 | 47 | 17 | 64 |
| 7 | 3.26[1]:1 | 30 | 48 | 15 | 69 |
| 8 | 5.70:1 | 30 | 47 | 16 | 66 |
| 9 | 13.4:1 | 30 | 58 | 11 | 81 |
| 10 | 56.3:1 | 30 | 53 | 5 | 91 |
| 11 | 100:1 | 30 | 49 | 5 | 90 |
| 12 | 6.5[2]:1 | 24 | 51 | 51 | 0 |
| 13 | 50[2]:1 | 60 | 55 | 46 | 13 |
| 14 | 100[3]:1 | 30 | 53 | 43 | 19 |

[1] p-PD was added as a 1% by weight aqueous solution.
[2] 1,3-phenylenediamine was used instead of p-PD.
[3] para-Anisidine was used instead of p-PD.

The data in Table 1 show the reduction in levels of protoanemonin as a result of adding p-PD, as a solid and as an aqueous solution, to aqueous monomer solution at various temperatures. The p-PD is effective at reducing the level of protoanemonin over a broad range of relative quantities and over a broad temperature range. The data also show that the meta-substituted phenylenediamine, 1,3-phenylenediamine, was not effective at reducing the level of PTA in the aqueous monomer solution. Also, para-anisidine which is a para-substituted monoamine, is shown to be ineffective at reducing the level of PTA in the aqueous monomer solution.

The data appearing in Table 2 show the effects of concentration of the aqueous monomer solution and were conducted in the same manner as the examples appearing in Table 1, except that the temperature for each example was 24° C. The concentrations (Conc.) reported in Table 2, below, are the concentrations of the monomer in aqueous solution. The aqueous monomer concentrations were controlled by diluting with deionized water, or adding glacial acrylic acid to aqueous acrylic acid prepared by vapor phase oxidation of propylene. The examples in Table 2 which were run at 100 percent concentration were conducted using glacial acrylic acid only.

TABLE 2

| Example | Conc. | Molar Ratio p-PD:PTA | PTA initial (ppm) | PTA final (ppm) | PTA reduction (%) |
|---|---|---|---|---|---|
| 15 | 10% | 4.4:1 | 15 | 6 | 60 |
| 16 | 32% | 2.9:1 | 44 | 16 | 64 |
| 17 | 48% | 3:1 | 102 | 23 | 77 |
| 18 | 74% | 5.1:1 | 62 | 22 | 65 |
| 19 | 87% | 6.7:1 | 20 | 15 | 25 |
| 20 | 100% | 1.9:1 | 33 | 30 | 9 |
| 21 | 100% | 50.1:1 | 29 | 28 | 3 |
| 22 | 100% | 1.9[4]:1 | 33 | 29 | 12 |

[4] 1,3-phenylenediamine was used instead of p-PD.

The data appearing in Table 2 show the effectiveness of p-PD in reducing the level of PTA in aqueous monomer solutions of varying concentration. In the glacial monomer, the p-PD is not effective at reducing the level of PTA. The data also show that the meta-substituted phenylenediamine, 1,3-phenylenediamine, was not effective at reducing the level of PTA in the glacial monomer.

The data appearing in Table 3 show the effects of several disubstituted phenylenediamine compounds (Diamine) on the level of PTA in aqueous monomer solutions. The examples appearing in Table 3 were conducted in the same manner as the examples appearing in Table 1, except that the temperature for each example was 24° C.

TABLE 3

| | Molar Ratio Diamine:PTA | PTA Initial (ppm) | PTA final (ppm) | PTA reduction (%) |
|---|---|---|---|---|
| Example 23: 1,4-Phenylenediamine | | | | |
| 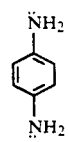 | 2.9:1 | 44 | 16 | 64 |
| Example 24: N-(4-Methoxyphenyl)-1,4-phenylenediamine hydrochloride | | | | |
| 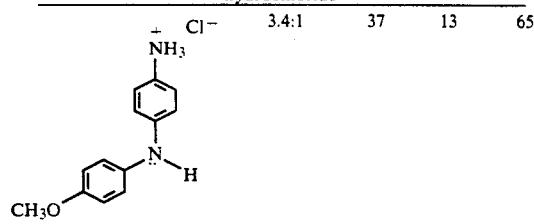 | 3.4:1 | 37 | 13 | 65 |
| Example 25: N,N-Dimethyl-1,4-phenylenediamine | | | | |
| 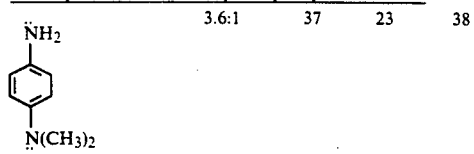 | 3.6:1 | 37 | 23 | 38 |
| Example 26: 2,5-Dimethyl-1,4-phenylenediamine | | | | |
| 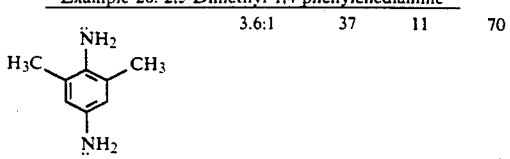 | 3.6:1 | 37 | 11 | 70 |

TABLE 3-continued

| | Molar Ratio Diamine:PTA | PTA Initial (ppm) | PTA final (ppm) | PTA reduction (%) |
|---|---|---|---|---|

Example 27: N,N-Diethyl-1,4-pheylenediamine

| | 3.6:1 | 37 | 31 | 16 |

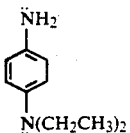

Example 28: N,N'-Diphenyl-1,4-phenylenediamine

| | 3.4:1 | 37 | 32 | 14 |

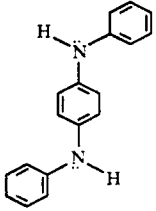

Example 29: 2,3,5,6-Tetramethyl-1,4-phenylenediamine

| | 2.2:1 | 38 | 38 | 0 |

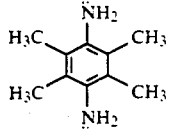

Example 30: N,N,N',N'-Tetramethyl-1,4-phenylenediamine

| | 2.2:1 | 38 | 38 | 0 |

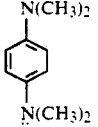

Example 31: 1,4-Phenylenediamine dihydrochloride

| | 2.6:1 | 48 | 7 | 85 |

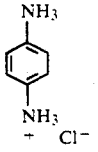

Example 32: N,N-Dimethyl-1,4-phenylenediamine hydrochloride

| | 2.6:1 | 48 | 24 | 50 |

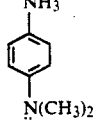

Example 33: N,N-Dimethyl-1,4-phenylenediamine sulfate

| | 2.6:1 | 48 | 25 | 48 |

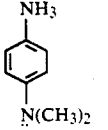

Example 34: 2-Methoxy-N⁴-phenyl-1,4-phenylenediamine

| | 3.4:1 | 38 | 27 | 30 |

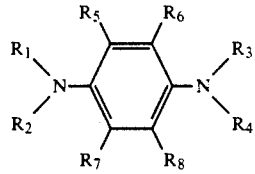

Example 35: 1,4,-Diaminoanthraquinone

| | 3.3:1 | 38 | 38 | 0 |

Example 36: 2-Methoxy-1,4-phenylenediamine sulfate hydrate

| | 2.7:1 | 48 | <1 | >98 |

The data appearing in Table 3 show that para-substituted phenylenediamines of formula (I, supra) are consistently effective at reducing the level of PTA in the aqueous monomer solutions.

What is claimed is:

1. A method of reducing the level of protoanemonin in an aqueous monomer solution comprising:
adding to the aqueous monomer solution an effective amount of one or more para-phenylenediamines having the following formula:

I wherein $R_1$, $R_2$, $R_3$ and $R_4$ are the same or different radical selected from hydrogen, methyl, ethyl, n-propyl, iso-propyl or methoxyphenyl with the proviso that at least one of $R_1$, $R_2$, $R_3$ and $R_4$ is hydrogen; $R_5$, $R_6$, $R_7$ and $R_8$ are the same or different radical selected from the group consisting of hydrogen, methyl, ethyl, n-propyl, iso-propyl, methoxy or ethoxy with the proviso that at least one of $R_5$, $R_6$, $R_7$ and $R_8$ is hydrogen; and salts thereof.

2. The method of claim 1 wherein at least two of $R_1$, $R_2$, $R_3$ and $R_4$ are hydrogen.

3. The method of claim 1 wherein at least two of $R_5$, $R_6$, $R_7$ and $R_8$ are hydrogen.

4. The method of claim 1 wherein the para-phenylenediamine is selected from 1,4-phenylenediamine, N-(4-methoxyphenyl)-1,4-phenylenediamine, N,N-dimethyl-1,4-phenylenediamine, 2,5-dimethyl-1,4-phenylenediamine, 2-methoxy-N⁴-phenyl-1,4-phenylenediamine, 2-methoxy-1,4-phenylenediamine or the hydrogen halide, sulfate or hydrogen sulfate salts thereof.

5. The method of claim 1 wherein the paraphenylenediamine is 1,4-phenylenediamine or the hydrogen halide, sulfate or hydrogen sulfate salts thereof.

6. The method of claim 1 wherein the paraphenylenediamine is N-(4-methoxyphenyl)-1,4-phenylenediamine or the hydrogen halide, sulfate or hydrogen sulfated salts thereof.

7. The method of claim 1 wherein the paraphenylenediamine is N,N-dimethyl-1,4-phenylenediamine or the hydrogen halide, sulfate or hydrogen sulfate salts thereof.

8. The method of claim 1 wherein the paraphenylenediamine is 2,5-dimethyl-1,4-phenylenediamine or the hydrogen halide, sulfate or hydrogen sulfate salts thereof.

9. The method of claim 1 wherein the paraphenylenediamine is 2-methoxy-$N^4$-phenyl-1,4-phenylenediamine or the hydrogen halide, sulfate or hydrogen sulfate salts thereof.

10. The method of claim 1 wherein the paraphenylenediamine is added to the aqueous monomer solution at a level of from about 0.3 to about 400 equivalents based on the level of protoanemonin present in said aqueous monomer solution.

11. The method of claim 1 wherein the paraphenylenediamine is added to the aqueous monomer solution at a level of from about 0.5 to about 300 equivalents based on the level of protoanemonin present in said aqueous monomer solution.

12. The method of claim 1 wherein the paraphenylenediamine is added to the aqueous monomer solution at a level of from about 0.7 to about 200 equivalents based on the level of protoanemonin present in said aqueous monomer solution.

13. The method of claim 1 wherein the aqueous monomer solution is an aqueous solution of acrylic acid.

14. The method of claim 1 wherein the aqueous monomer solution is an aqueous solution of methacrylic acid.

15. The method of claim 1 wherein the aqueous monomer solution is from about 10 percent to about 95 percent by weight monomer.

16. The method of claim 1 wherein the aqueous monomer solution is from about 15 percent to about 90 percent by weight monomer.

17. The method of claim 1 wherein the aqueous monomer solution is from about 20 percent to about 65 percent by weight monomer.

* * * * *